US012714395B2

(12) United States Patent
Doron et al.

(10) Patent No.: US 12,714,395 B2
(45) **Date of Patent: *Aug. 25, 2026**

(54) SYSTEM AND METHOD FOR GUIDING POSITIONING AND ORIENTING OF AN ULTRASOUND PROBE

(71) Applicant: ULTRASIGHT LTD, Nes Ziona (IL)

(72) Inventors: Adam Itzhak Doron, Rehovot (IL); Itay Kezurer, Rehovot (IL)

(73) Assignee: ULTRASIGHT LTD, Nes Ziona (IL)

( * ) Notice: Subject to any disclaimer, the term of this patent is extended or adjusted under 35 U.S.C. 154(b) by 433 days.

This patent is subject to a terminal disclaimer.

(21) Appl. No.: 17/715,128

(22) Filed: Apr. 7, 2022

(65) Prior Publication Data

US 2022/0338836 A1 Oct. 27, 2022

Related U.S. Application Data

(63) Continuation-in-part of application No. 17/235,972, filed on Apr. 21, 2021, now abandoned.

(51) Int. Cl.
*A61B 8/00* (2006.01)
*A61B 8/08* (2006.01)

(52) U.S. Cl.
CPC .............. *A61B 8/4245* (2013.01); *A61B 8/08* (2013.01); *A61B 8/461* (2013.01); *A61B 8/488* (2013.01); *A61B 8/5207* (2013.01)

(58) Field of Classification Search
None
See application file for complete search history.

(56) References Cited

U.S. PATENT DOCUMENTS

2004/0019270 A1* 1/2004 Takeuchi ................. A61B 8/14 600/407
2005/0020903 A1 1/2005 Krishnan
2010/0329521 A1* 12/2010 Beymer ............... G06V 10/761 600/443
2015/0265205 A1 9/2015 Rosenbek et al.
2015/0305689 A1 10/2015 Gourmelon et al.
2016/0007955 A1 1/2016 Kuroiwa et al.
2016/0019270 A1 1/2016 Jones et al.
(Continued)

FOREIGN PATENT DOCUMENTS

WO 2019046521 A1 3/2019

OTHER PUBLICATIONS

International Search Report of Application No. PCT/IL2021/050252 mailed on Mar. 8, 2021.
(Continued)

*Primary Examiner* — Jonathan Cwern
(74) *Attorney, Agent, or Firm* — Heidi Brun Associates Ltd.; Heidi M. Brun

(57) ABSTRACT

Systems and methods for positioning and orienting an ultrasound probe include receiving a dataset derived from the ultrasound probe, wherein the dataset comprises at least one dataset obtained during a pulsed Doppler mode operation of the probe; analyzing the dataset to identify a current position and orientation of the probe relative to a target position and orientation, wherein the target position and orientation align the probe to correctly acquire a selected view of a body part; and conveying the current position and orientation of the probe relative to the target position and orientation.

12 Claims, 10 Drawing Sheets

(56) References Cited

U.S. PATENT DOCUMENTS

| | | | | |
|---|---|---|---|---|
| 2017/0215842 | A1 | 8/2017 | Ryu | |
| 2017/0360403 | A1 | 12/2017 | Rothberg et al. | |
| 2019/0328317 | A1* | 10/2019 | Mochizuki | A61B 8/06 |
| 2019/0354856 | A1* | 11/2019 | Kezurer | A61B 8/483 |
| 2019/0362740 | A1 | 11/2019 | Hauptman et al. | |
| 2020/0077940 | A1 | 3/2020 | Srivastava et al. | |
| 2020/0113542 | A1 | 4/2020 | Perrey et al. | |
| 2020/0113544 | A1 | 4/2020 | Huepf | |
| 2021/0052253 | A1* | 2/2021 | Cadieu | A61B 8/5223 |
| 2021/0161510 | A1* | 6/2021 | Sasaki | A61B 8/06 |

OTHER PUBLICATIONS

International Search Report of Application No. PCT/IL2022/050369 mailed on Jul. 27, 2022.

Supplementary European Search Report mailed in corresponding European application 22791253.2 on Jan. 29, 2025.

* cited by examiner

Figure 6:
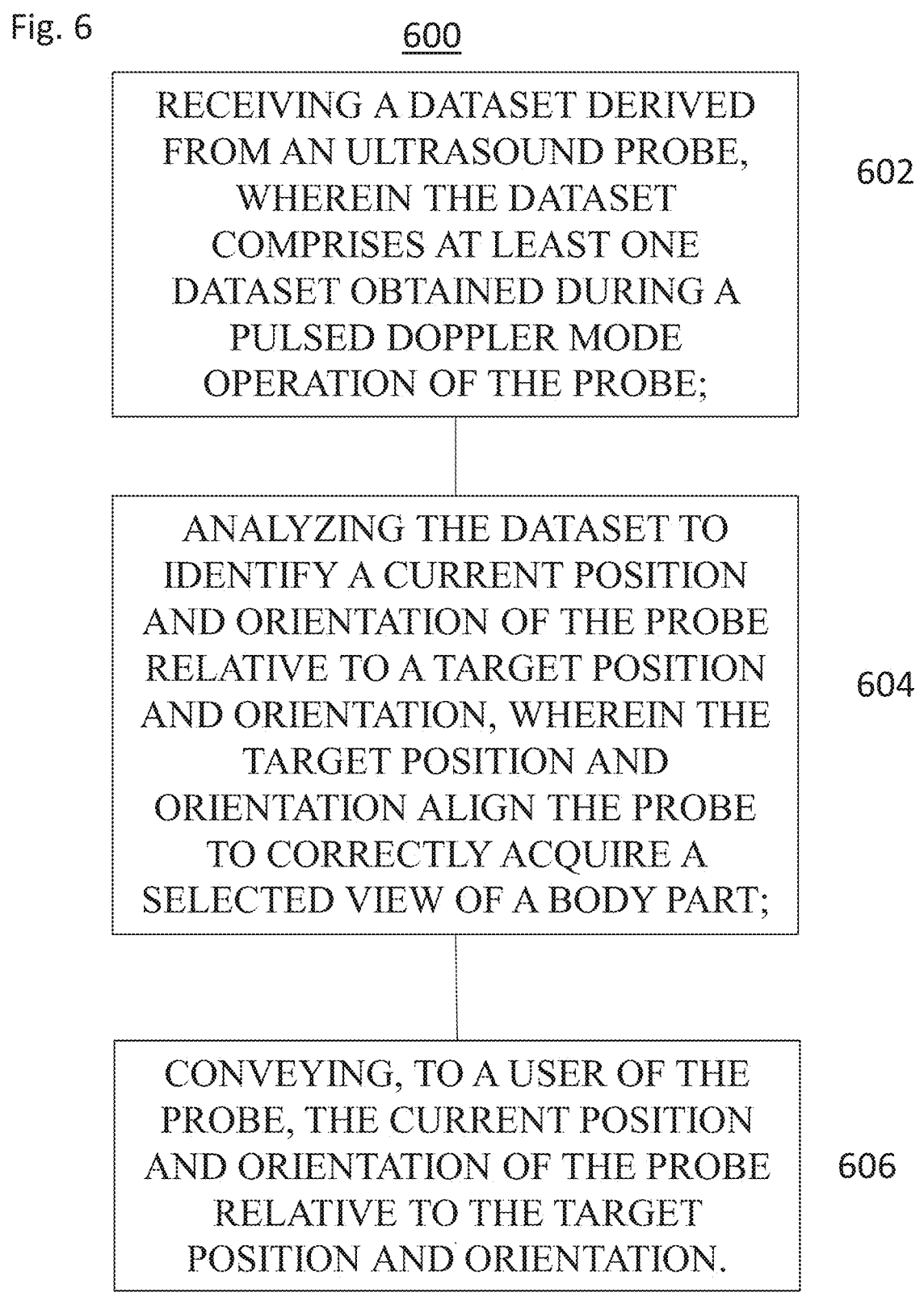

RECEIVING A DATASET DERIVED FROM AN ULTRASOUND PROBE, WHEREIN THE DATASET COMPRISES AT LEAST ONE DATASET OBTAINED DURING A PULSED DOPPLER MODE OPERATION OF THE PROBE;

602

ANALYZING THE DATASET TO IDENTIFY A CURRENT POSITION AND ORIENTATION OF THE PROBE RELATIVE TO A TARGET POSITION AND ORIENTATION, WHEREIN THE TARGET POSITION AND ORIENTATION ALIGN THE PROBE TO CORRECTLY ACQUIRE A SELECTED VIEW OF A BODY PART;

604

CONVEYING, TO A USER OF THE PROBE, THE CURRENT POSITION AND ORIENTATION OF THE PROBE RELATIVE TO THE TARGET POSITION AND ORIENTATION.

606

SYSTEM AND METHOD FOR GUIDING POSITIONING AND ORIENTING OF AN ULTRASOUND PROBE

CROSS-REFERENCE TO RELATED APPLICATIONS

This application is a continuation in part of U.S. patent application Ser. No. 17/235,972 filed 21 Mar. 2021 and now abandoned, which is incorporated by reference herein in its entirety.

FIELD OF THE INVENTION

The present invention relates to the field of guiding positioning and orienting of an ultrasound probe, and more particularly, to systems and methods using data obtained in a pulsed Doppler mode for generating visual cues for guiding positioning and orienting of an ultrasound probe.

BACKGROUND OF THE INVENTION

Ultrasound scanners are used extensively in a wide range of clinical scenarios. When used by experienced professionals, the utility of point-of-care ultrasound scanning for assessing organ anatomy and function has been well established. However, in some important clinical circumstances (e.g., in primary care offices, intensive care units, emergency rooms, remote settings, etc.) in which a rapid assessment of organ anatomy and function may facilitate patient care, a professional experienced at point-of-care ultrasound scanning may not be immediately available. Ultrasound scanners are known which can operate in different modes, such as pulsed Doppler mode.

SUMMARY OF THE INVENTION

Some embodiments of the present invention may provide a system for positioning and orienting of an ultrasound probe. The system may include: a computer processor; and one or more sets of instructions which, when executed, cause the computer processor to: receive or determine a dataset indicating a type, a direction and a measure of motion required to bring an ultrasound probe from its current position and orientation to its target position and orientation, wherein the target position and orientation align the ultrasound probe to correctly acquire a selected view of a body part; generate, based on at least a portion of the dataset, one or more images each including one or more visual cues indicating the type, the direction and the measure of motion required to bring the ultrasound probe from its current position and orientation to its target position and orientation; and cause a presentation of the one or more images on a display.

In some embodiments, each of the one or more images may include: a first visual cue indicating the target position and orientation of the ultrasound probe; and a second visual cue indicating the current position and orientation of the ultrasound probe relative to the target position and orientation of the ultrasound probe.

In some embodiments: a relative position and orientation between the second visual cue and the first visual cue are indicating the type and the direction of motion required to bring the ultrasound probe from its current position and orientation to its target position and orientation; and a distance between a specified point on the second visual cue and a corresponding specified point on the first visual cue is indicating the measure of motion required to bring the ultrasound probe from its current position and orientation to its target position and orientation.

In some embodiments, the first visual cue may include: a cross figure having two bars which are perpendicular to each other and intersecting at an intersection point; wherein the cross figure represents a proximal end of the ultrasound probe in its target position and orientation; wherein the intersection point represents a central longitudinal axis of the ultrasound probe in its target position and orientation; and wherein a plane defined by the bars represents a plane that is perpendicular to the central longitudinal axis of the ultrasound probe its target position and orientation.

In some embodiments, the first visual cue may further include a visual marker which position corresponds to a position of a corresponding physical marker on the ultrasound probe.

In some embodiments, the second visual cue may include: a 2D projection of a 3D representation of the ultrasound probe in its current position and orientation; and a second cross figure having two second bars which are perpendicular to each other and intersecting at a second intersection point; wherein the second cross figure represents the proximal end of the ultrasound probe in its current position and orientation; wherein the second intersection point represents the central longitudinal axis of the ultrasound probe in its current position and orientation; and wherein a plane defined by the second bars represents a plane that is perpendicular to the central longitudinal axis of the ultrasound probe its current position and orientation.

In some embodiments, the second visual cue may further include a second visual marker which position corresponds to a position of a corresponding physical marker on the ultrasound probe.

In some embodiments, the second visual cue may include an arrow, wherein a shape of the arrow indicates the type of motion, a direction of the arrow indicates the direction of motion and a size of the arrow indicates the measure of motion required to bring the ultrasound probe from its current position and orientation to its target position and orientation.

In some embodiments, the second visual cue may include a text indicator having numeral values to quantify the measure of motion required to bring the ultrasound probe from its current position and orientation to its target position and orientation.

In some embodiments, the one or more sets of instructions, when executed, cause the computer processor further to: receive at least one ultrasound image acquired by the ultrasound probe in the current position and orientation thereof; and feed the at least one ultrasound image and the selected view of the body part as an input into a neural network, wherein the neural network being implemented on the computer processor and configured to output the dataset.

Some embodiments of the present invention may provide a method of positioning and orienting of an ultrasound probe, the method may include: receiving or determining, by a computer processor, a dataset indicating a type, a direction and a measure of motion required to bring an ultrasound probe from its current position and orientation to its target position and orientation, wherein the target position and orientation align the ultrasound probe to correctly acquire a selected view of a body part; generating, by the computer processor, based on at least a portion of the dataset, one or more images each including one or more visual cues indicating the type, the direction and the measure of motion required to bring the ultrasound probe from its current position and orientation to its target position and orientation; and causing, by the computer processor, a presentation of the one or more images on a display.

In some embodiments, each of the one or more images may include: a first visual cue indicating the target position and orientation of the ultrasound probe; and a second visual cue indicating the current position and orientation of the ultrasound probe relative to the target position and orientation of the ultrasound probe.

In some embodiments: a relative position and orientation between the second visual cue and the first visual cue are indicating the type and the direction of motion required to bring the ultrasound probe from its current position and orientation to its target position and orientation; and a distance between a specified point on the second visual cue and a corresponding specified point on the first visual cue is indicating the measure of motion required to bring the ultrasound probe from its current position and orientation to its target position and orientation.

In some embodiments, the first visual cue may include: a cross figure having two bars which are perpendicular to each other and intersecting at an intersection point; wherein the cross figure represents a proximal end of the ultrasound probe in its target position and orientation; wherein the intersection point represents a central longitudinal axis of the ultrasound probe in its target position and orientation; and wherein a plane defined by the bars represents a plane that is perpendicular to the central longitudinal axis of the ultrasound probe its target position and orientation.

In some embodiments, the first visual cue may further include a visual marker which position corresponds to a position of a corresponding physical marker on the ultrasound probe.

In some embodiments, the second visual cue may include: a 2D projection of a 3D representation of the ultrasound probe in its current position and orientation; and a second cross figure having two second bars which are perpendicular to each other and intersecting at a second intersection point; wherein the second cross figure represents the proximal end of the ultrasound probe in its current position and orientation; wherein the second intersection point represents the central longitudinal axis of the ultrasound probe in its current position and orientation; and wherein a plane defined by the second bars represents a plane that is perpendicular to the central longitudinal axis of the ultrasound probe its current position and orientation.

In some embodiments, the second visual cue may further include a second visual marker which position corresponds to a position of a corresponding physical marker on the ultrasound probe.

In some embodiments, the second visual cue may include an arrow, wherein a shape of the arrow indicates the type of motion, a direction of the arrow indicates the direction of motion and a size of the arrow indicates the measure of motion required to bring the ultrasound probe from its current position and orientation to its target position and orientation.

In some embodiments, the second visual cue may include a text indicator having numeral values to quantify the measure of motion required to bring the ultrasound probe from its current position and orientation to its target position and orientation.

In some embodiments, the method may further include: receiving, by the computer processor, the at least one ultrasound image acquired by the ultrasound probe in the current position and orientation thereof; and feeding, by the computer processor, the at least one ultrasound image and the selected view of the body part as an input into a neural network, wherein the neural network being implemented on the computer processor and configured to output the dataset.

According to an embodiment of the invention, a method for positioning and orienting an ultrasound probe includes receiving a dataset derived from the ultrasound probe, wherein the dataset includes at least one dataset obtained during a pulsed Doppler mode operation of the probe; analyzing the dataset to identify a current position and orientation of the probe relative to a target position and orientation, wherein the target position and orientation align the probe to correctly acquire a selected view of a body part; and conveying, to a user of the probe, the current position and orientation of the probe relative to the target position and orientation.

According to some embodiments, the dataset includes an image derived from signals obtained by the ultrasound probe.

According to some embodiments, the dataset is received by monitoring a display in communication with the ultrasound probe.

According to some embodiments, the at least one dataset obtained during a pulsed Doppler mode operation of the probe includes an image and Doppler information.

According to some embodiments, the image is augmented with the Doppler information.

According to some embodiments, analyzing the dataset includes using an artificial intelligence process.

According to some embodiments, the analyzing includes analyzing a motion within the body part based on pulsed Doppler mode information.

According to some embodiments, the motion is a motion of fluid within the body part.

According to some embodiments, the artificial intelligence process outputs at least one of: a current position and orientation of the ultrasound probe relative to the selected view; and an indication of a quality of an image produced by the ultrasound probe at its current position and orientation, wherein the quality of the image corresponds to whether the selected view has been achieved.

According to some embodiments, the conveying includes generating, based on at least a portion of the dataset, one or more images each including one or more visual cues indicating the current position and orientation of the probe; and causing a presentation of the one or more images on a display.

According to some embodiments, the one or more visual cues includes at least one of an indication of a type, a direction, and a measure of motion required to bring the probe from its current position and orientation to its target position and orientation.

According to some embodiments, the conveying includes presenting an image quality indication scale on a display.

According to an embodiment, there is provided a method for correcting a position and orientation of an ultrasound probe, the method including: receiving an image derived from the ultrasound probe, wherein the image is superimposed with fluid flow information obtained during a pulsed Doppler mode operation of the probe; analyzing the image to determine a current position and orientation of the probe relative to a target position and orientation, wherein the target position and orientation align the probe to correctly acquire a selected view of a body part; and conveying, to a user of the probe; the current position and orientation of the probe relative to the target position and orientation; and an indication of a quality of the image as being the selected view.

According to an embodiment, there is disclosed a system for positioning and orienting an ultrasound probe, the system including: a computer processor; and a memory including one or more sets of instructions which, when executed, cause the computer processor to: receive a dataset derived from the ultrasound probe, wherein the dataset includes at least one dataset obtained during a pulsed Doppler mode operation of the probe; analyze the dataset to identify a current position and orientation of the probe relative to a target position and orientation, wherein the target position and orientation align the probe to correctly acquire a selected view of a body part; and convey, to a user of the probe, the current position and orientation of the probe relative to the target position and orientation.

According to some embodiments, the processor executes an artificial intelligence process to analyze the dataset.

According to some embodiments, the analyzing comprises analyzing a motion within the body part based on pulsed Doppler mode information.

According to some embodiments, the artificial intelligence process outputs at least one of: a current position and orientation of the ultrasound probe relative to the selected view; and an indication of a quality of an image produced by the ultrasound probe at its current position and orientation, wherein the quality of the image corresponds to whether the selected view has been achieved.

According to some embodiments, the conveying includes generating, based on at least a portion of the dataset, one or more images each including one or more visual cues indicating the current position and orientation of the probe; and causing a presentation of the one or more images on a display.

According to some embodiments, the conveying further includes displaying an image quality indication scale.

According to some embodiments, the one or more visual cues includes at least one of an indication of a type, a direction, and a measure of motion required to bring the probe from its current position and orientation to its target position and orientation.

These, additional, and/or other aspects and/or advantages of the present invention are set forth in the detailed description which follows: possibly inferable from the detailed description; and/or learnable by practice of the present invention.

BRIEF DESCRIPTION OF THE DRAWINGS

For a better understanding of embodiments of the invention and to show how the same can be carried into effect, reference will now be made, purely by way of example, to the accompanying drawings in which like numerals designate corresponding elements or sections throughout. In the accompanying drawings:

FIG. 6 is a flowchart of a method according to an embodiment of the invention;

Figure 1:
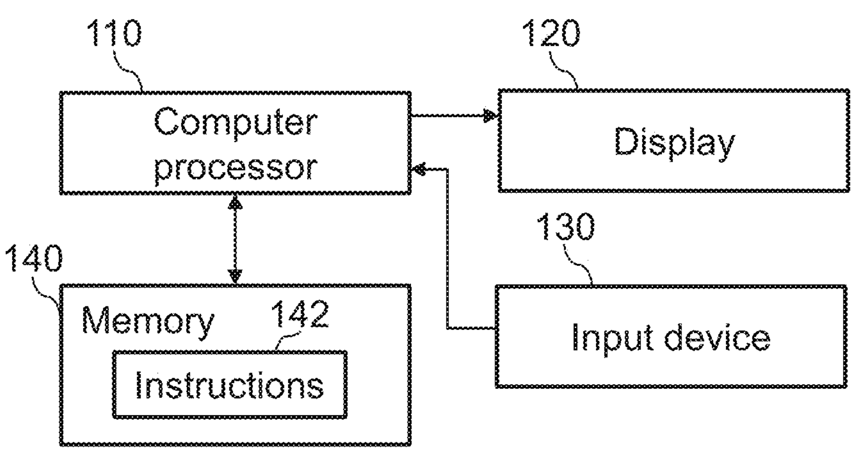
FIG. 1 is a block diagram of a system for guiding positioning and orienting of an ultrasound probe, according to some embodiments of the invention.

It will be appreciated that, for simplicity and clarity of illustration, elements shown in the figures have not necessarily been drawn to scale. For example, the dimensions of some of the elements may be exaggerated relative to other elements for clarity. Further, where considered appropriate, reference numerals may be repeated among the figures to indicate corresponding or analogous elements.

DETAILED DESCRIPTION OF THE INVENTION

In the following description, various aspects of the present invention are described. For purposes of explanation, specific configurations and details are set forth in order to provide a thorough understanding of the present invention. However, it will also be apparent to one skilled in the art that the present invention can be practiced without the specific details presented herein. Furthermore, well known features can have been omitted or simplified in order not to obscure the present invention. With specific reference to the drawings, it is stressed that the particulars shown are by way of example and for purposes of illustrative discussion of the present invention only and are presented in the cause of providing what is believed to be the most useful and readily understood description of the principles and conceptual aspects of the invention. In this regard, no attempt is made to show structural details of the invention in more detail than is necessary for a fundamental understanding of the invention, the description taken with the drawings making apparent to those skilled in the art how the several forms of the invention can be embodied in practice.

Before at least one embodiment of the invention is explained in detail, it is to be understood that the invention is not limited in its application to the details of construction and the arrangement of the components set forth in the following description or illustrated in the drawings. The invention is applicable to other embodiments that can be practiced or carried out in various ways as well as to combinations of the disclosed embodiments. Also, it is to be understood that the phraseology and terminology employed herein is for the purpose of description and should not be regarded as limiting.

Unless specifically stated otherwise, as apparent from the following discussions, it is appreciated that throughout the specification discussions utilizing terms such as "processing." "computing," "calculating," "determining," "enhancing." or the like, refer to the action and/or processes of a computer or computing system, or similar electronic computing device, that manipulates and/or transforms data represented as physical, such as electronic, quantities within the computing system's registers and/or memories into other data similarly represented as physical quantities within the computing system's memories, registers or other such information storage, transmission or display devices. Any of the disclosed modules or units can be at least partially implemented by a computer processor.

Reference is now made to FIG. 1, which is a block diagram of a system 100 for guiding positioning and orienting of an ultrasound probe, according to some embodiments of the invention.

Figure 2:
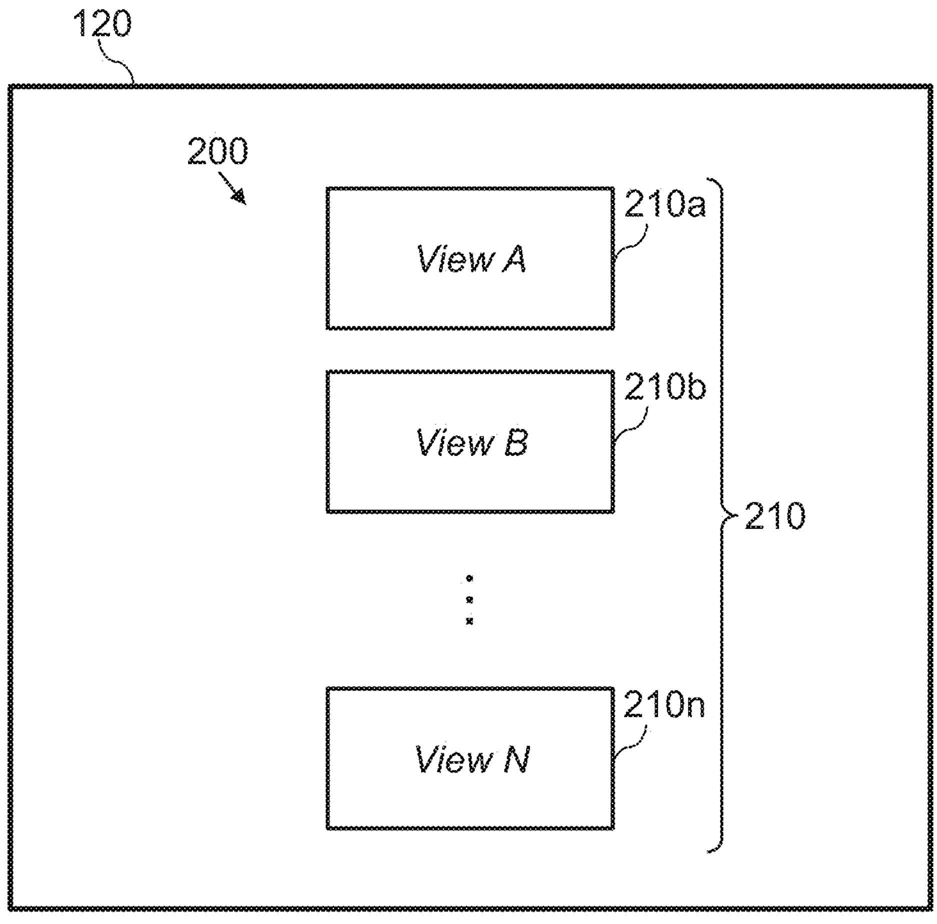
FIG. 2 is a schematic illustration of a display presenting data indicating a set of possible views of a body part of a subject scannable using an ultrasound probe, according to some embodiments of the invention.

Reference is also made to FIG. 2, which is a schematic illustration of a display 120 presenting data indicating a set 210 of possible views 210*a* . . . 210*n* of a body part of a subject scannable using an ultrasound probe, according to some embodiments of the invention.

Figure 3:
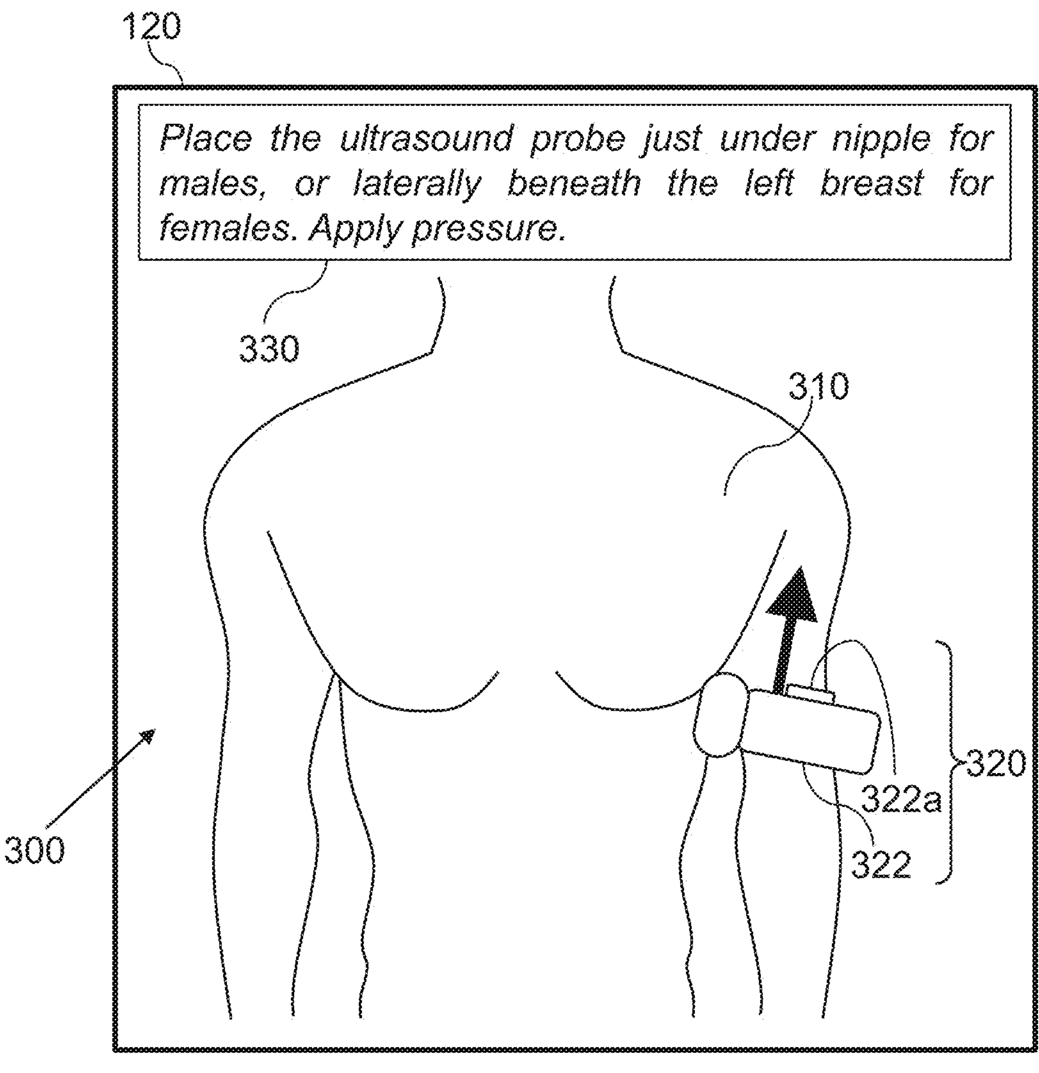
FIG. 3 is a schematic illustration of a display presenting an image including visual cues indicating a target position and orientation of the ultrasound probe with respect to at least a portion of a subject body, according to some embodiments of the invention.

Reference is also made to FIG. 3, which is a schematic illustration of a display 120 presenting an image 300 including visual cues 310, 320 indicating a target position and orientation of the ultrasound probe with respect to at least a portion of a subject body, according to some embodiments of the invention.

Reference is also made to FIGS. 4A-4I, which are schematic illustrations of a display 120 presenting an image 400 including visual cues 410, 420 indicating a type, direction and measure of motion required to bring the ultrasound probe from its current position and orientation to the target position and orientation thereof, according to some embodiments of the invention.

According to some embodiments of the present invention, system 100 may include a computer processor 110, a display 120, an input device 130 and a memory 140 including one or more sets of instructions 142. One or more sets of instructions 142, when executed, may cause computer processor 110 to perform functions described herein.

According to some embodiments, computer processor 110 may generate an image 200 that includes data indicating a set 210 of possible views 210*a* . . . 210*n* of a body part of a subject scannable using an ultrasound probe (e.g., as shown in FIG. 2). Image 200 may, for example, include illustrations of views 210*a* . . . 210*n*, a list of views 210*a* . . . 210*n*, etc. Computer processor 110 may cause a presentation of image 200 on display 120. Set 210 may include at least some data collected during a pulsed Doppler mode operation of the ultrasound probe.

According to some embodiments, computer processor 110 may receive a selection of a view of set 210 of possible views 210*a* . . . 210*n* of the body part. For example, computer processor 110 may receive the selection using input device 130.

According to some embodiments, computer processor 110 may generate an image 300 (e.g., as shown in FIG. 3). Image 300 may include one or more visual cues indicating a target position and orientation of the ultrasound probe with respect to at least a portion of a subject body. The target position and orientation align the ultrasound probe to correctly acquire the selected view of the body part.

In some embodiments, image 300 may include a first visual cue 310 including a visual representation of at least a portion of the subject body (e.g., a trunk of the subject body as schematically shown in FIG. 3).

In some embodiments, image 300 may include a second visual cue 320 including a visual representation 322 of the ultrasound probe in its target position and orientation with respect to the subject body. In some embodiments, visual representation 322 of the ultrasound probe may include a two-dimensional (2D) projection of a three-dimensional (3D) representation of the ultrasound probe in its target position and orientation (e.g., as shown in FIG. 3).

In some embodiments, the ultrasound probe (e.g., the physical ultrasound probe) may include a physical marker on one of its lateral sides. In some embodiments, visual representation 322 of the ultrasound probe may include a visual marker 322*a* which position corresponds to the position of the corresponding physical marker on the ultrasound probe.

In some embodiments, image 300 may include a text indicator 330 including written instructions describing, for example, the target position and orientation of the ultrasound probe with respect to the subject body (e.g., as shown in FIG. 3), or other written instructions.

According to some embodiments, computer processor 110 may receive a dataset indicating a type (e.g., sliding, rotation, tilting, rocking), a direction (e.g., upwards, downwards, rightwards, leftwards, clockwise, counterclockwise, etc.) and a measure (e.g., inches, degrees, quaternions, coordinates, etc.) of motion required to bring the ultrasound probe from its current position and orientation to the target position and orientation thereof.

According to some embodiments, computer processor 110 may generate the dataset indicating the type, the direction and the measure of motion required to bring the ultrasound probe from its current position and orientation to the target position and orientation thereof. In some embodiments, computer processor 110 may generate the dataset based on the selected view of the body part and at least one ultrasound image acquired by the ultrasound probe in the current position and orientation thereof. The at least one ultrasound image may be received from, for example, an ultrasound device. In some embodiments, computer processor 110 may determine the dataset using, e.g., a trained neural network being implemented on computer processor 110. For example, computer processor 110 may feed the at least one ultrasound image and the selected view of the body part as an input to the neural network and the neural network may output the dataset.

According to some embodiments, computer processor 110 may generate, based on the dataset, one or more images 400 (e.g., as shown in FIGS. 4A-4I). Each of the one or more images 400 may include one or more visual cues indicating, e.g., the type, the direction and/or the measure of motion required to bring the ultrasound probe from its current position and orientation to the target position and orientation thereof. Computer processor 110 may cause a presentation of one or more images 400 on display 120.

In some embodiments, each of one or more images 400 may include a first visual cue 410 indicating the target position and orientation of the ultrasound probe. In some embodiments, first visual cue 410 may include a cross FIG. 412 having two bars 412*a*, 412*b* which are perpendicular to each other and intersecting at an intersection point 412*c*. Cross FIG. 412 may represent, for example, a proximal end of the ultrasound probe, wherein intersection point 412*c* may represent a central longitudinal axis of the ultrasound probe in its target position and orientation, and a plane defined by bars 412*a*, 412*b* of cross FIG. 412 may represent a plane that is perpendicular to the central longitudinal axis of the ultrasound probe in its target position and orientation. In some embodiments, first visual cue 410 may include a visual marker 414 (e.g., schematically indicated in FIGS. 4A-4I by two arches) which position corresponds to the position of the corresponding physical marker on the ultrasound probe.

In some embodiments, each of the one or more images 400 may include a second visual cue 420 indicating the current position and orientation of the ultrasound probe relative to the target position and orientation of the ultrasound probe. In some embodiments, second visual cue 420 may include a 2D projection of a 3D representation of the ultrasound probe 422 in its current position and orientation. In some embodiments, second visual cue 420 may include a cross FIG. 424 having two bars 424*a*, 424*b* perpendicular to each other and intersecting at an intersection point 424*c*. Cross FIG. 424 may represent the proximal end of the ultrasound probe in its current position and orientation, wherein intersection point 424*c* may represent the central longitudinal axis of the ultrasound probe in its current position and orientation, and a plane defined by bars 424*a*, 424*b* of cross FIG. 424 may represent the plane that is perpendicular to the central longitudinal axis of the ultrasound probe in its current position and orientation. In some embodiments, second visual cue 420 may include a visual marker 426 (e.g., schematically indicated in FIGS. 4A-4I by two arches) which position corresponds to the position of the corresponding physical marker on the ultrasound probe.

A relative position and orientation between second visual cue 420 and first visual cue 410 may indicate the type, the direction and/or the measure of motion required to bring the ultrasound probe from its current position and orientation to its target position and orientation.

Figures 4A, 4B, 4C:
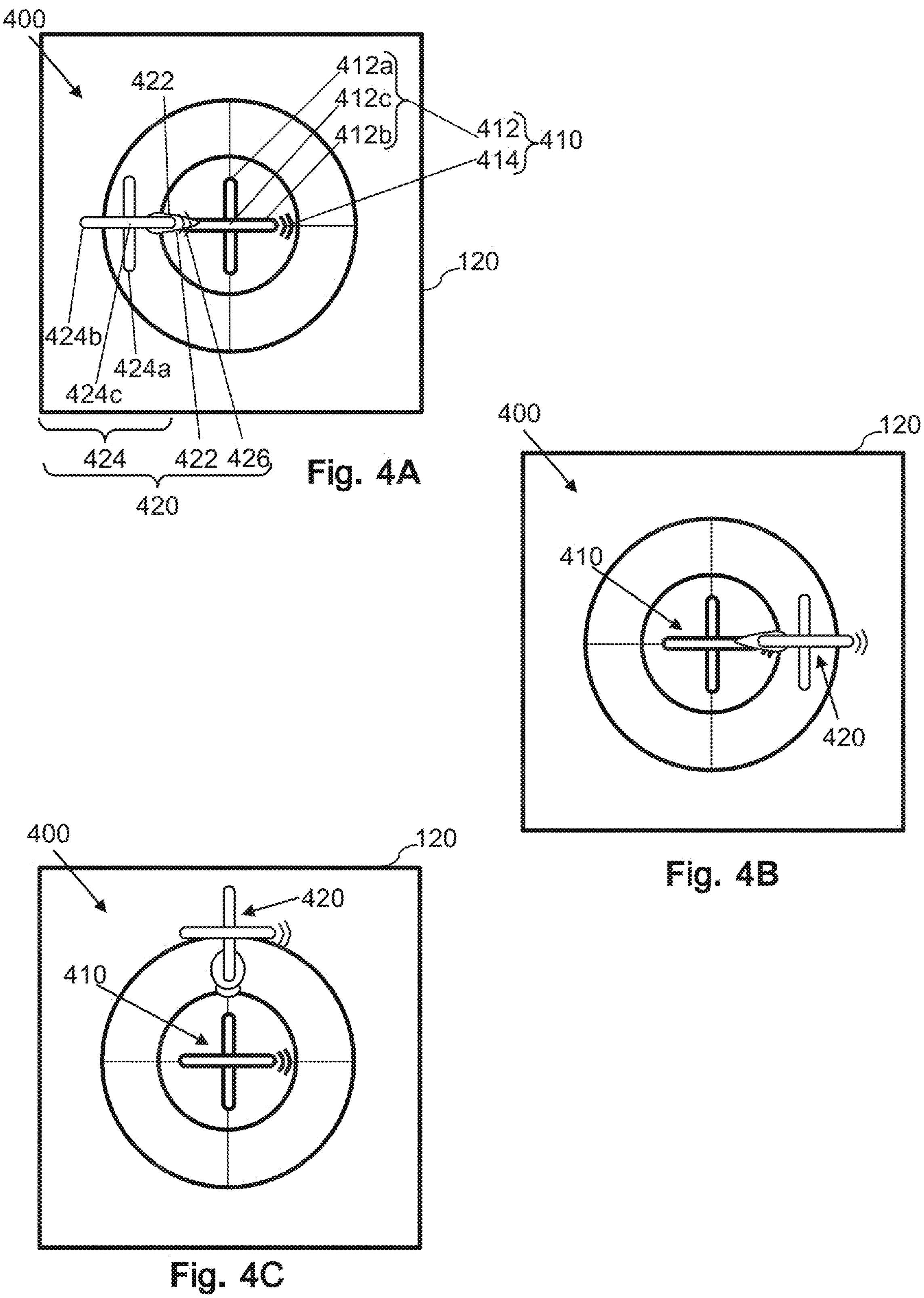
FIGS. 4A-4I are schematic illustrations of a display presenting an image including visual cues indicating a type, direction and measure of motion required to bring the ultrasound probe from its current position and orientation to the target position and orientation thereof, according to some embodiments of the invention.

For example, the relative position and orientation between second visual cue 420 and first visual cue 410 as schematically shown in FIG. 4A indicates that the ultrasound probe should be slid or otherwise moved rightward with respect to its current position and orientation to bring the ultrasound probe to its target position and orientation.

In another example, the relative position and orientation between second visual cue 420 and first visual cue 410 as schematically shown in FIG. 4B indicates that the ultrasound probe should be slid or otherwise moved leftward with respect to its current position and orientation to bring the ultrasound probe to its target position and orientation.

In another example, the relative position and orientation between second visual cue 420 and first visual cue 410 as schematically shown in FIG. 4C indicates that the ultrasound probe should be slid or otherwise moved downward with respect to its current position and orientation to bring the ultrasound probe to its target position and orientation.

Figures 4D, 4E, 4F:
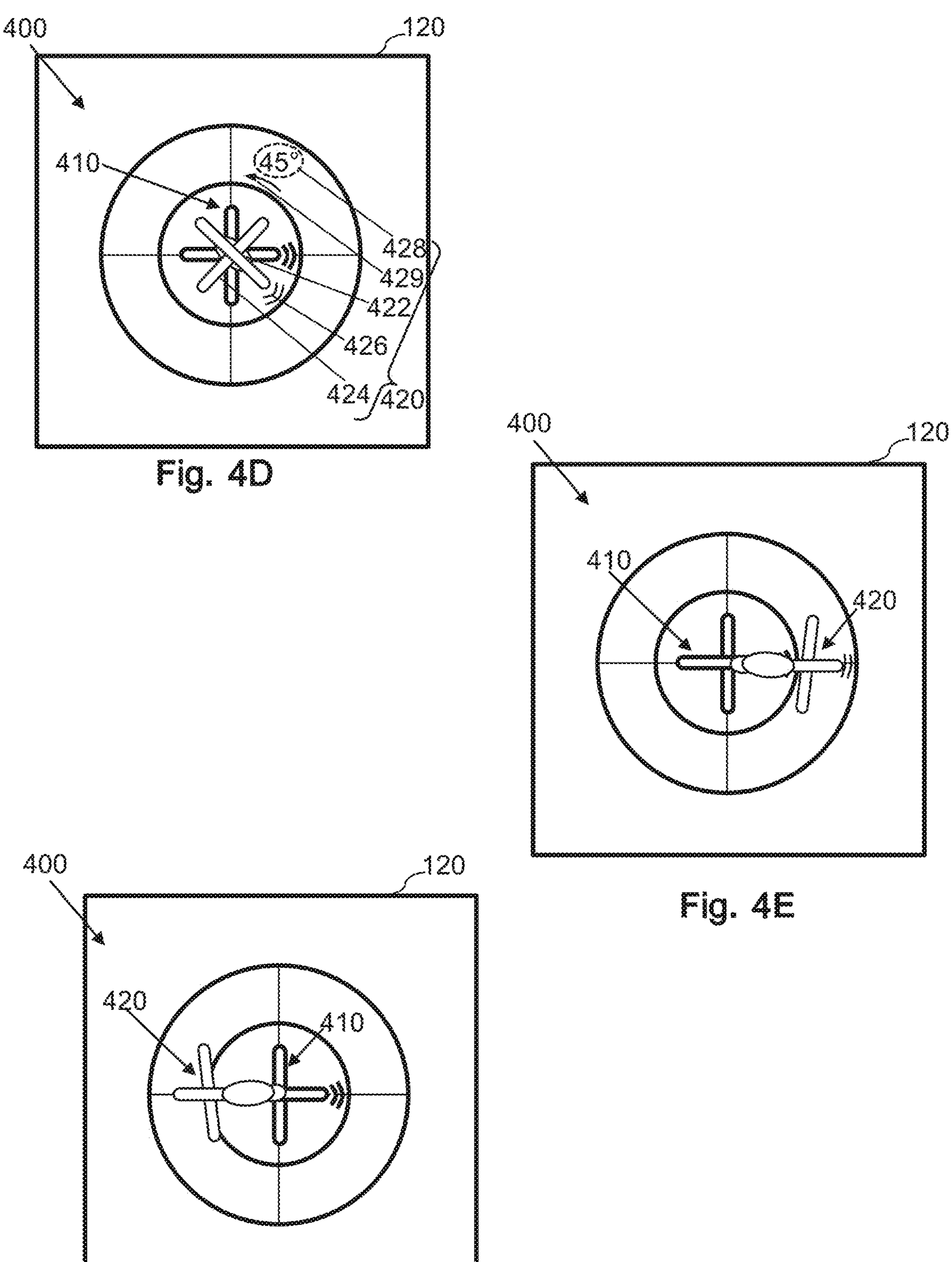

In another example, the relative position and orientation between second visual cue 420 and first visual cue 410 as schematically shown in FIG. 4D indicates that the ultrasound probe should be rotated counterclockwise with respect to its current position and orientation to bring the ultrasound probe to its target position and orientation.

In another example, the relative position and orientation between second visual cue 420 and first visual cue 410 as schematically shown in FIG. 4E indicates that the ultrasound probe should be tilted leftwards with respect to its current position and orientation to bring the ultrasound probe to its target position and orientation.

In another example, the relative position and orientation between second visual cue 420 and first visual cue 410 as schematically shown in FIG. 4F indicates that the ultrasound probe should be tilted rightwards with respect to its current position and orientation to bring the ultrasound probe to its target position and orientation.

Figures 4G, 4H, 4I:
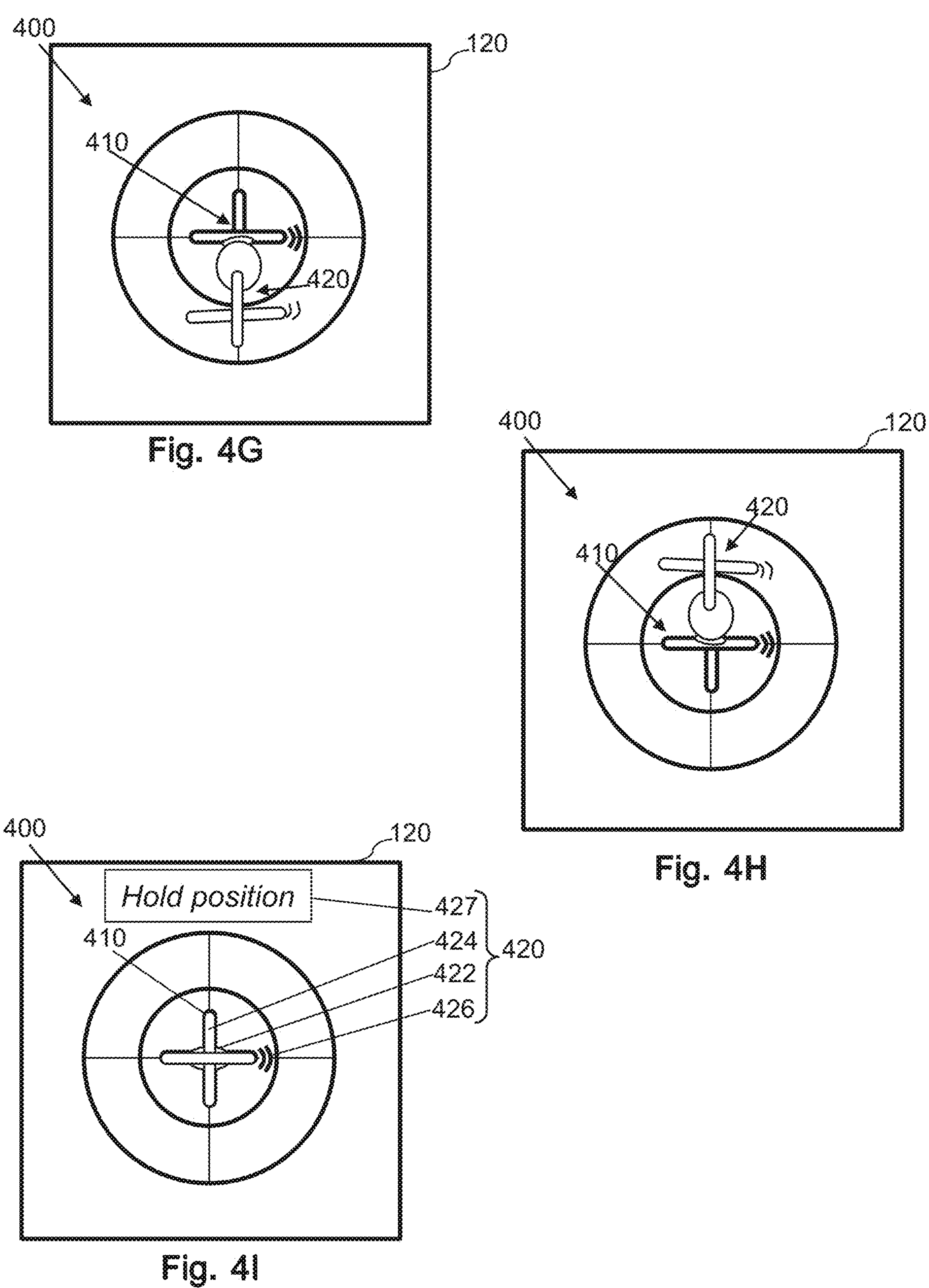

In another example, the relative position and orientation between second visual cue 420 and first visual cue 410 as schematically shown in FIG. 4G indicates that the ultrasound probe should be tilted upwards with respect to its current position and orientation to bring the ultrasound probe to its target position and orientation.

In another example, the relative position and orientation between second visual cue 420 and first visual cue 410 as schematically shown in FIG. 4H indicates that the ultrasound probe should be tilted downwards with respect to its current position and orientation to bring the ultrasound probe to its target position and orientation.

In another example, the relative position and orientation between second visual cue 420 and first visual cue 410 as schematically shown in FIG. 4I indicates that the ultrasound probe is in its target position and orientation. In some embodiments, second visual cue 420 may include an indicator 427 instructing to hold the position and orientation of the ultrasound probe (e.g., text indicator 427 as schematically shown in FIG. 4I). In some embodiments, image 400 may include a progress bar (not shown) or other visual progress indicator (e.g., a percentage, hour-glass, etc.) indicating an ultrasound scan progress.

In some embodiments, the distance between a specified point on second visual cue 420 and a corresponding point on first visual cue 410 may indicate the measure of motion (e.g., inches, degrees, quaternions, coordinates, etc.) required to bring the ultrasound probe from its current position and orientation to its target position and orientation. For example, a distance between (i) intersection point 424*c* of cross FIG. 424 of second visual cue 420 and (ii) intersection point 414*c* of cross FIG. 412 of first visual cue 410 may indicate the measure of motion required to bring the ultrasound probe from its current position and orientation to its target position and orientation. In some embodiments, second visual cue 420 may include a text indicator 428 with numeral values to quantify the measure of motion required to bring the ultrasound probe from its current position and orientation to its target position and orientation. For example, as schematically shown in FIG. 4D, text indictor 428 indicates that the ultrasound probe should be rotated counterclockwise by 45° with respect to its current position and orientation to bring the ultrasound probe to its target position and orientation. It is noted that text indicator 428 is shown only in FIG. 4D and not shown in FIGS. 4A-4C and FIGS. 4E-4I for the sake of clarity.

In some embodiments, second visual cue 420 may include an arrow 429, wherein a shape of the arrow may indicate the type of motion, a direction of the arrow may indicate the direction of motion and/or a size of the arrow may indicate the measure of motion required to bring the ultrasound probe from its current position and orientation to its target position and orientation. For example, as schematically shown in FIG. 4D, arrow 429 indicates that the ultrasound probe should be rotated counterclockwise with respect to its current position and orientation to bring the ultrasound probe to its target position and orientation. It is noted that arrow 429 is shown only in FIG. 4D and not shown in FIGS. 4A-4C and FIGS. 4E-4I for the sake of clarity. It is also noted that different combinations of the visual cues as described herein with respect to FIGS. 4A-4I are also possible.

According to some embodiments, computer processor 110 may generate, based on the dataset, one or more sound cues indicating the type, the direction and the measure of motion required to bring the ultrasound probe from its current position and orientation to the target position and orientation thereof. For example, the one or more sound cues may include one or more voice or audio instructions, such as, e.g., “rotate the ultrasound probe left”, “move the ultrasound probe 4 inches rightwards”, “hold the position of the ultrasound probe”, etc. In another example, the one or more sound cues may include a first sound indicating the ultrasound probe is in the target position and orientation thereof and that the ultrasound probe is acquiring the ultrasound images. In another example, the one or more sound cues may include a second sound indicating that the ultrasound probe completed the acquiring of the ultrasound images.

Figure 5:
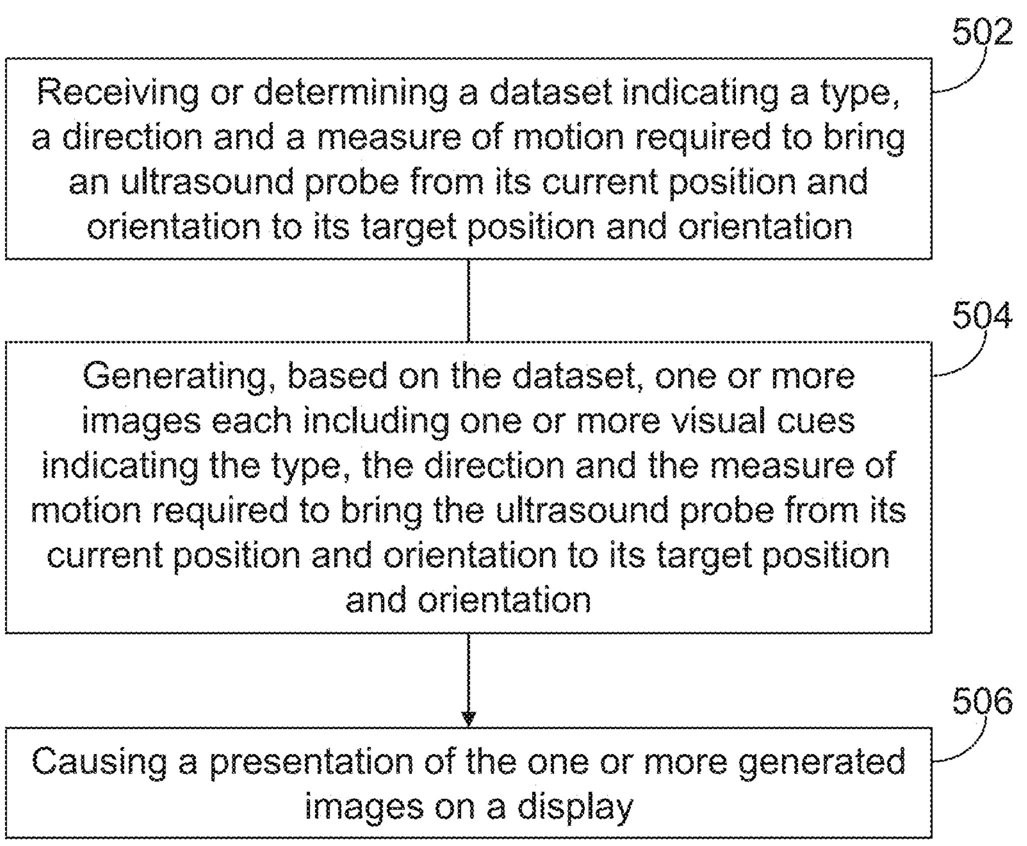
FIG. 5 is a flowchart of a method of guiding positioning and orienting of an ultrasound probe, according to some embodiments of the invention.

Reference is now made to FIG. 5, which is a flowchart of a method of guiding positioning and orienting of an ultrasound probe, according to some embodiments of the invention.

In some embodiments, the method may include receiving or determining 502, by a computer processor, a dataset indicating at least one of a type, a direction and a measure of motion required to bring an ultrasound probe from its current position and orientation to its target position and orientation, wherein the target position and orientation align the ultrasound probe to correctly acquire a selected view of a body part. For example, computer processor 110 and dataset described above with respect to FIG. 1.

The method may include generating 504, by the computer processor, based on the dataset, one or more images, wherein each of the one or more images includes one or more visual cues indicating the type, the direction and/or the measure of motion required to bring the ultrasound probe from its current position and orientation to its target position and orientation. For example, visual cues 410, 420 described above with respect to FIGS. 4A-4I.

The method may include causing 506, by the computer processor, a presentation of the one or more generated images on a display. For example, display 120 described above with respect to FIG. 1.

Figure 7:
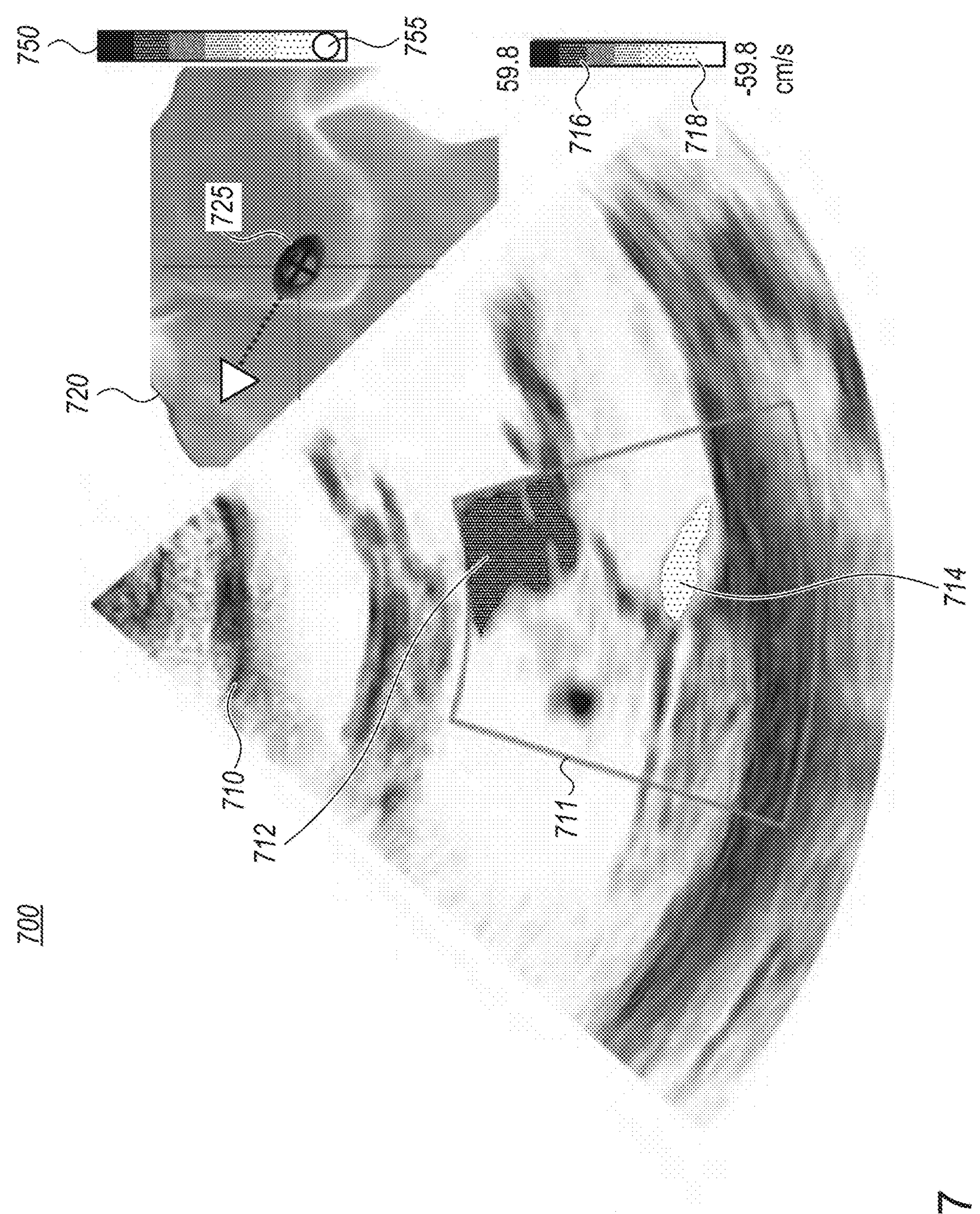
FIG. 7 is a schematic illustration of a display according to an embodiment of the invention.
Figure 8:
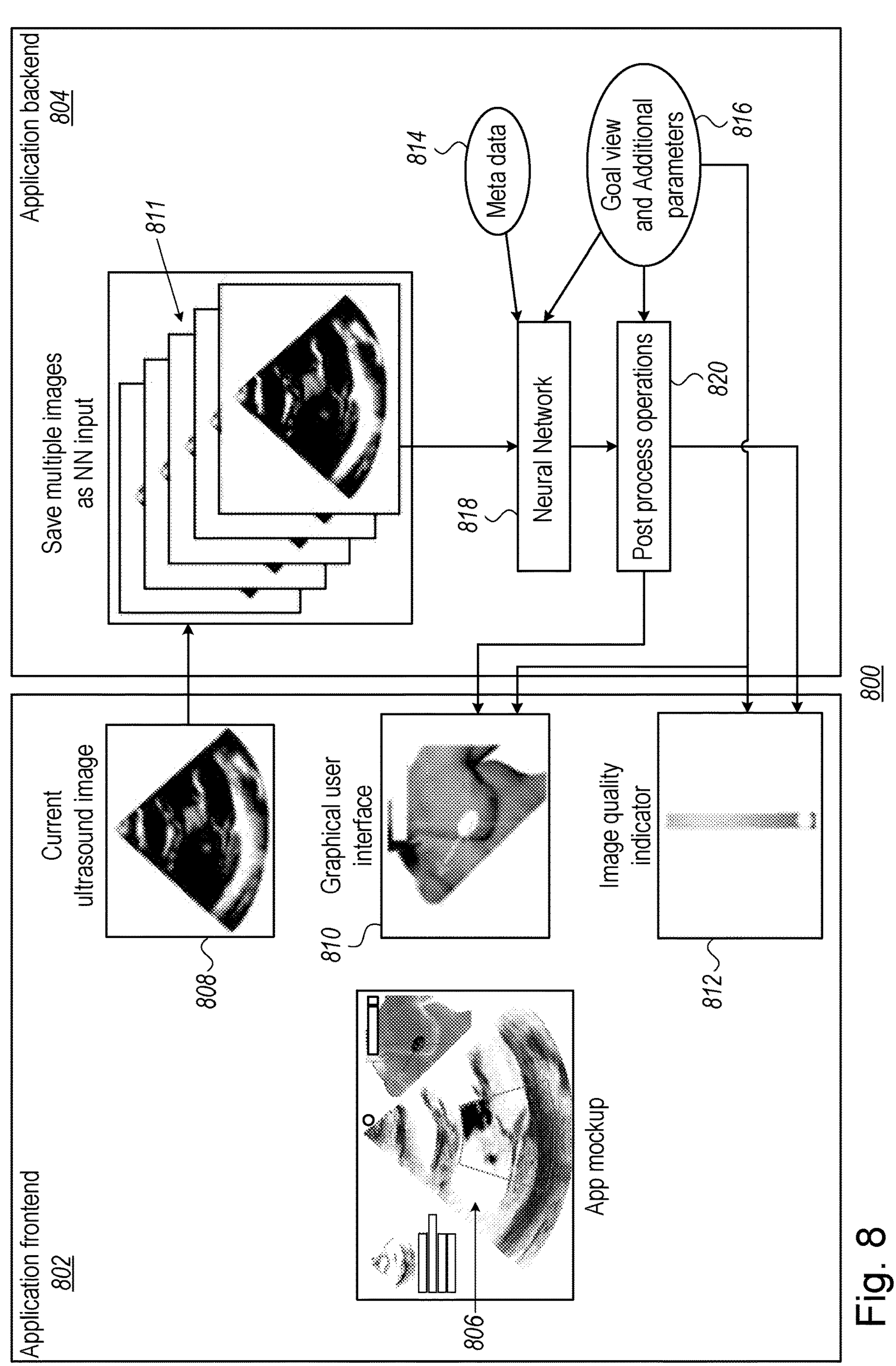
FIG. 8 is a schematic illustration of a system according to an embodiment of the invention.

With reference now to FIGS. 6, 7, and 8, embodiments of the invention may use data obtained in a pulsed Doppler mode operation of an ultrasound probe to identify a position and orientation of the ultrasound probe and potentially assist a user in correcting or adjusting a position and orientation of the probe to correctly acquire a selected/desired view of a body part. An ultrasound probe operating in pulsed Doppler mode uses the principle that moving objects affect the properties of sound waves. By sending short and quick pulses of sound, the ultrasound machine (e.g. probe+software) may be able to measure the velocity of movement within the body, for example moving fluid (e.g. blood), movement of the lungs during breathing, and movement along the digestive system, all in real time at specific locations within the body. Because blood flows in accordance with the periodic cardiac cycle (e.g. the process of contraction and relaxation involved in one heartbeat), data and/or images obtained by a probe operating in pulsed Doppler mode may be analyzed to account for variations in the way an ultrasound image may appear. For example, computer vision systems may incorrectly determine the position and orientation of an ultrasound probe due to the way in which an image obtained at that position and orientation may change as a consequence of the specific timing in the cardiac cycle: in some images the heart may appear larger, and in others, smaller (the morphology of the heart varies drastically at different times along the cardiac cycle, the volume of the left ventricle for example changes in a healthy heart by more than 50-70% along the cycle). These variations/distortions due to temporal degrees of freedom in ultrasound images can fool computer vision systems into determining an incorrect position and orientation of the ultrasound probe. In embodiments of the present invention, using implicit or explicit information of the blood flow can assist an artificial intelligence in accounting for changes that are due to the specific timing along the cycle.

FIG. 6 is a flowchart of a method 600 for positioning and orienting an ultrasound probe. Method 600 may include receiving (602) a dataset derived from the ultrasound probe. A dataset derived from an ultrasound probe may be a dataset directly obtained from an ultrasound probe, or indirectly obtained. For example, a dataset directly obtained from the ultrasound probe may be a time series of transducer signal data, e.g. a series of reflected frequency measurements. A dataset obtained indirectly from an ultrasound probe may include an image (or plurality of images) derived from measurements obtained by the ultrasound probe. Such an image may be derived by processing software/hardware and may be displayed on a computer display in communication (e.g. wired communication) the ultrasound probe. Embodiments of the invention may monitor such a display (e.g. using computer vision techniques) in order to receive the dataset/images.

According to a preferred embodiment, the received dataset includes at least one dataset obtained during a pulsed Doppler mode operation of the probe. A dataset obtained during a pulsed Doppler mode operation of the probe may include Doppler information/data and may include an image containing or augmented with the Doppler information. An image augmented with Doppler information may be for example, the kind of image obtained during a B-mode operation of an ultrasound probe superimposed with (e.g. edited by software to indicate) colored regions indicating the flow of fluid (e.g. the Doppler information). For example, an image/dataset augmented with Doppler information may indicate regions (e.g. pixels or datapoints) where fluid is flowing away from the probe by associating a first color with those regions (or "tagging" the relevant data, e.g. with a string), for example blue. In an image derived from the probe, blue regions may therefore indicate that at the point in time the probe was operating, those regions contained fluid (e.g. blood) which was moving in a direction away from the probe. Similarly, regions where fluid is flowing towards the probe may be associated with a second color, such as red. An indication of the velocity of the fluid may be given by assigning shades of colors in a gradual scale corresponding to the speed, for example dark red for fast flowing fluid (e.g. 19 cm/s) moving toward the probe and lighter red for slower flowing fluid in a direction towards the probe (e.g. 4.9 cm/s). Similarly velocity for fluid moving away from the probe may be assigned by taking a blue color spectrum and distributing shades according to a slow to fast range (e.g. 1.5-7.1 cm/s) of speeds.

Method 600 may include analyzing (604) the dataset to identify a current position and orientation of the probe relative to a target position and orientation. A target position and orientation may be such as to represent a required position and orientation which would align the probe to correctly acquire a selected view of a body part, e.g. a four chamber view of the heart. A user of the probe (or, for example, a machine guided process such as through computer numeric control (CNC)) may alter, adjust, or otherwise move the probe in order to bring its position and orientation into conformity with the target position and orientation, and thus align the probe so as to obtain the desired view. According to some embodiments, analyzing the dataset may include using an artificial intelligence (AI) process, for example, a neural network trained on a set of training images (e.g. a training corpus or large collection of images). The artificial intelligence process may have been previously trained in a supervised manner, or an unsupervised manner. The artificial intelligence process may have been trained using labelled training data, for example ultrasound datasets (or images derived from such datasets) which have been correlated (e.g. labelled) with specific locations and/or orientations and/or views imaged by the probe. Training of the AI process in accordance with embodiments of the invention may allow the AI process to output indications about position and orientation of the ultrasound probe which are decoupled from temporal degrees of freedom in ultrasound images; for example images of the heart taken at the same probe location at different times can look different and may be erroneously interpreted by an AI algorithm as being taken from different probe positions. As the rate and direction of blood flow is driven by the periodic cardiac cycle, guidance in pulsed-Doppler-mode holds significantly more information regarding each frame's timing along the cardiac cycle than a B-mode ultrasound image. In addition, as there is an abundance of blood vessels in the body, images of pulsed-Doppler-mode hold such information even when the heart is not in the image.

An artificial intelligence process may be a neural network (NN). A neural network may include neurons or nodes organized into layers, with links between neurons transferring output between neurons. Aspects of a NN may be weighed, e.g. links may have weights, and training may involve adjusting weights. A positive weight may indicate an excitatory connection, and a negative weight may indicate an inhibitory connection. A NN may be executed and represented as formulas or relationships among nodes or neurons, such that the neurons, nodes, or links are "virtual", represented by software and formulas, where training or executing a NN is performed, for example, by a conventional computer or GPU (such as device 100 in FIG. 1).

According to some embodiments, the artificial intelligence process may analyze a motion in the received dataset, e.g. within the body part imaged by the probe. The motion may be analyzed based on pulsed Doppler mode information received as part of the dataset. For example, the artificial intelligence process may receive Doppler enhanced/augmented images obtained by monitoring a display in communication with the ultrasound probe: motion may then be inferred, for example by identifying colored regions in the monitored image corresponding to a velocity of motion towards/away from the probe. The motion could be due to a motion of a fluid flowing through the body part with some velocity, for example the flow of blood through the body part.

According to some embodiments, method 600 may include outputting by the AI process at least one of: a current position and orientation of the ultrasound probe relative to the selected view; and an indication of a quality of an image produced by the ultrasound probe at its current position and orientation, wherein the quality of the image corresponds to whether the selected view has been achieved. The current position and orientation relative to the selected view may be conveyed to a user in the ways discussed herein. The current position and orientation relative to the selected view may be a current position and orientation of the ultrasound probe compared to a position and orientation required to achieve the selected/target view of a body part. An indication of a quality of an image may refer to an "exactness" of an alignment of the ultrasound probe with a target position and orientation required to obtain a selected view of a body part, and whether or not this selected view has been achieved. In other words, the AI process outputs an indication of a quality of an image produced by the ultrasound probe at its current position and orientation as compared to the selected view. For example, a high quality image may be one which is obtained when the ultrasound probe is in exactly the right position and orientation required to obtain a selected view of a body part, for example a parasternal long axis view (PLAX) of the heart or an apical 4C (four chamber) view of the heart. A low quality image may be one obtained at an ultrasound probe position and orientation which is far removed from a required/target position and orientation. Image quality as used herein may not necessarily refer to image aberrations, for example a pixelation of the ultrasound image, but as described a measure of how accurately the position and orientation of the ultrasound probe producing the image in question corresponds to a target position and orientation required to obtain a goal/selected view of a body part. In identifying spatial and temporal degrees of freedom, embodiments of the invention may improve positioning of ultrasound probes compared to existing methods by providing guidance which takes account of this spatial and temporal relationship. According to some embodiments, method 600 includes identifying the current position and orientation of the probe relative to the target position and orientation based on at least one of the spatial degree of freedom and the temporal degree of freedom.

Method 600 may include conveying (606), e.g. to a user of the probe, the current position and orientation of the probe relative to the target position and orientation. For example, and according to some embodiments, conveying may include generating, based on at least a portion of the dataset, one or more images each including one or more visual cues indicating the current position and orientation (and, in some embodiments the target position and orientation) of the probe, and causing a presentation of the one or more images on a display. The visual cues may be, for example, cues such as those depicted in FIGS. 4A-4I. Conveying may include showing a graphic representation of the position and orientation (P&O) of the probe, and/or a graphic representation of the target position and orientation: a user may then manipulate the probe to bring it from its current P&O to the target P&O.

Alternatively, or complimentarily, conveying may include presenting an image quality indication scale (e.g. scale 750 in FIG. 7) on a display. As discussed above, an image quality indication may refer to a measure of fit/alignment of the probe P&O with a target P&O required to produce a selected view of a body part. Probe P&O and resultant image quality may be linked to motion within the body, for example a probe may be in the correct P&O to obtain a PLAX view of the heart, but motion of the lungs during breathing obscures the heart and so results in a lower quality image as compared to the selected PLAX view: thus, whilst the P&O of the probe would ordinarily be correct, the quality of the image is low because at that point in time the view as imaged by the probe is not the selected/desired view. A quality indication scale may be a continuous scale, and may include a graphical element (e.g. 755 in FIG. 7) such as a circle which may "slide" on the scale (e.g. up and down) as the determined image quality changes. Accordingly, a user may make fine adjustments to the P&O of the probe in order to obtain an acceptable image quality, guided by the action of the slider on the scale.

Conveying may also include providing one or more visual cues relating to at least one of an indication of a type, a direction, and a measure of motion required to bring the probe from its current P&O to its target P&O, for example by showing arrows indicating a direction of translational and/or rotational movement which the user of the probe should follow to correctly align the probe.

According to some embodiments, there is provided a method for correcting a position and orientation of an ultrasound probe. The method may include receiving an image derived from the ultrasound probe, for example an image superimposed with fluid flow information obtained during a pulsed Doppler mode operation of the probe. As described above, an image superimposed with fluid flow information obtained during a pulsed Doppler mode operation of the probe may include colored regions indicating flow towards and/or away from the probe, and may give an indication of the velocity of the fluid.

The method may further include analyzing the image to determine a current position and orientation of the probe relative to a target position and orientation, wherein the target position and orientation is such as to align the probe to correctly acquire a selected view of a body part.

The determining, for example by an AI process, may take into account a position and orientation of the probe based on a relationship between a temporal degree of freedom and at least one spatial degree of freedom, at the captured point in time within the periodic cycle of fluid flow. For example, an inferred point in a periodic fluid cycle (e.g. inferred from Doppler information) may be factored into outputting a position and orientation and/or image quality indication.

The method may also include conveying, for example to a user of the probe, the current position and orientation of the probe relative to the target position and orientation and an indication of a quality of the image as being the selected view. For example, the quality indication may be high if the image is (e.g. corresponds to) the selected view, and the quality indication may be low if the image is not (e.g. does not show or relate to) the selected view.

FIG. 7 shows a schematic illustration of an exemplary display view 700 which may be conveyed to a user of the ultrasound probe. Display view 700 may be displayed on a computer display, such as a display in communication (e.g. wired or wireless connection) with the ultrasound probe. Display view 700 may include an image 710 derived from signals (e.g. ultrasound measurements) obtained at the ultrasound probe. Display view 700 may for example show a parasternal long axis (PLAX) view of the heart. Display 700 may also include a graphic representation of the current position and orientation 725 of the probe relative to a subject 720 being observed (e.g. human body).

Display view 700 may include a tutorial (not shown) e.g. textual or graphical instructions on how to move the probe from its current position and orientation to the target position and orientation.

Display view 700 may also include an image quality indication, such as an image quality scale 750. Image quality scale 750 may include a graphical element such as a slider 755 to indicate to a user a quality of image 710 as obtained at the current P&O 725 of the probe. For example, if the desired view is an apical four chamber view of the heart, but the captured image does not currently show a clear view of all the chambers, the image quality scale may indicate a low image quality. A low image quality may be corrected by moving the ultrasound probe to the target position and orientation, and slider 755 may move correspondingly so that a user can make final adjustments in order to obtain the selected view of the body part.

A region 711 of image 710 may be augmented (e.g. superimposed) with Doppler information. The augmentation may be performed by at least one processor in communication with the probe and display. Display view 700 may show image 710 as having regions indicating motion, such as fluid motion. Display view 700 may indicate regions 712 which are moving towards the probe, for example by displaying such regions in a first color, e.g. red (in the drawings, hatching and stippling has been used rather than color). A scale on the display may indicate a velocity of the motion, such as a color scale of shades with shades 716 representing speeds in a direction towards the probe e.g. a positive velocity ranging from approximately 0 to 59.8 cm/s. Display view 700 may indicate regions 714 which are moving away from the probe, for example by displaying such regions in a second color, e.g. blue. The scale on the display may indicate a velocity of the motion, such as a color scale of shades with shades 718 representing speeds in a direction away from the probe e.g. a negative velocity ranging from approximately 0 to −59.8 cm/s. The motion may be a motion of a fluid, for example blood. Embodiments of the invention may monitor a display such as is shown in FIG. 7 (e.g. a display which includes Doppler information) and may use computer vision techniques, screen grabs and/or screen captures of the displayed images as inputs to an analysis process, such as an artificial intelligence process like a neural network. The AI process may then analyze the images and doppler information to output the current position 725 of the probe and/or an image quality indication on image quality scale 750.

According to some embodiments, there is provided a system which may perform one or more steps of the methods herein described. For example, and according to an embodiment, a system for positioning and orienting an ultrasound probe includes a computer processor and a memory containing one or more sets of instructions which, when executed, cause the computer processor to: receive a dataset derived from the ultrasound probe, wherein the dataset includes at least one dataset obtained during a pulsed Doppler mode operation of the probe; analyze the dataset to identify a current position and orientation of the probe relative to a target position and orientation, wherein the target position and orientation align the probe to correctly acquire a selected view of a body part; and convey, to a user of the probe, the current position and orientation of the probe relative to the target position and orientation.

The system may be a system such as that described in FIG. 1, and may operate in conjunction with a display in communication with the ultrasound probe, for example by direct monitoring of the display or by interfacing with the communications feed for the display. The processor of the system may execute an artificial intelligence process to analyze the dataset, as described above.

FIG. 8 shows an architecture of a system 800 according to some embodiments of the invention. System 800 may be embodied as a software as a service (SAAS) product, such as an application/app, which may be deployed on or in conjunction with existing ultrasound processing platforms, such as ultrasound probe systems developed by Philips (Koninklijke Philips N.V.). General Electric Company, Clarius, Butterfly, Exo and Fujifilm SonoSite. For example, embodiments of the invention may work alongside any of the EPIQ, Affiniti, CX50, Lumify, and/or Sparq as developed by Philips; the Vscan, Vscan Air, Vscan Extend, Venue, Venue Fit, Venue Go, Vivid, Versana, NextGen LOGIQ, and/or LOGIQ as developed by GE; Clarius handheld probes; the Butterfly IQ and IQ+; and/or Sonosite PX, Sonosite LX, Sonosite S, Sonosite EDGE, Sonosite X-PORTE, and/or Sonosite M-Turbo as developed by Sonosite.

System 800 may include a frontend 802 which may be viewed by a user, for example on a display device. Frontend 802 may display a display view 806 such as is described for display view 700 of FIG. 7. The display view may be augmented with Doppler information. Display view 806 may include a current ultrasound image 808, a graphical user interface 810 and/or an image quality indicator 812 (as described above with respect to scale 750).

An application backend 804 may receive a plurality of ultrasound images 808 and may save these for an input 811 to a neural network 818. Neural network 818 may also receive metadata 814, which may include such data as timestamps, Doppler data, ultrasound signal data (e.g. frequency, reflected intensity), and patient weight, height, age, gender, known pathologies etc. Neural network 818 may also receive a goal/target view 816 (e.g. a desired view selected by user input) and additional parameters such as required image quality Neural network 818 may analyze these inputs, for example to determine a current position and orientation of the probe relative to a target position and orientation which would achieve the goal view, as well as to determine an image quality indication.

Post process operations 820 may be performed in order to convey guidance to a user via the graphical user interface and image quality indicator of the frontend. Post process operations may include any logic that is performed in order to convey the navigation output and quality to the user. The input to this logic may include an output of the neural network. For example, smoothing of the neural network output may be performed before displaying it to the user, e.g. by taking an average over multiple outputs to minimize anomalous results.

Aspects of the present invention are described above with reference to flowchart illustrations and/or portion diagrams of methods, apparatus (systems) and computer program products according to embodiments of the invention. It will be understood that each portion of the flowchart illustrations and/or portion diagrams, and combinations of portions in the flowchart illustrations and/or portion diagrams, can be implemented by computer program instructions. These computer program instructions can be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or portion diagram or portions thereof.

These computer program instructions can also be stored in a computer readable medium that can direct a computer, other programmable data processing apparatus, or other devices to function in a particular manner, such that the instructions stored in the computer readable medium produce an article of manufacture including instructions which implement the function/act specified in the flowchart and/or portion diagram portion or portions thereof. The computer program instructions can also be loaded onto a computer, other programmable data processing apparatus, or other devices to cause a series of operational steps to be performed on the computer, other programmable apparatus or other devices to produce a computer implemented process such that the instructions which execute on the computer or other programmable apparatus provide processes for implementing the functions/acts specified in the flowchart and/or portion diagram portion or portions thereof.

The aforementioned flowchart and diagrams illustrate the architecture, functionality, and operation of possible implementations of systems, methods and computer program products according to various embodiments of the present invention. In this regard, each portion in the flowchart or portion diagrams can represent a module, segment, or portion of code, which includes one or more executable instructions for implementing the specified logical function(s). It should also be noted that, in some alternative implementations, the functions noted in the portion can occur out of the order noted in the figures. For example, two portions shown in succession can, in fact, be executed substantially concurrently, or the portions can sometimes be executed in the reverse order, depending upon the functionality involved. It will also be noted that each portion of the portion diagrams and/or flowchart illustration, and combinations of portions in the portion diagrams and/or flowchart illustration, can be implemented by special purpose hardware-based systems that perform the specified functions or acts, or combinations of special purpose hardware and computer instructions.

In the above description, an embodiment is an example or implementation of the invention. The various appearances of "one embodiment", "an embodiment", "certain embodiments" or "some embodiments" do not necessarily all refer to the same embodiments. Although various features of the invention can be described in the context of a single embodiment, the features can also be provided separately or in any suitable combination. Conversely, although the invention can be described herein in the context of separate embodiments for clarity, the invention can also be implemented in a single embodiment. Certain embodiments of the invention can include features from different embodiments disclosed above, and certain embodiments can incorporate elements from other embodiments disclosed above. The disclosure of elements of the invention in the context of a specific embodiment is not to be taken as limiting their use in the specific embodiment alone. Furthermore, it is to be understood that the invention can be carried out or practiced in various ways and that the invention can be implemented in certain embodiments other than the ones outlined in the description above.

The invention is not limited to those diagrams or to the corresponding descriptions. For example, flow need not move through each illustrated box or state, or in exactly the same order as illustrated and described. Meanings of technical and scientific terms used herein are to be commonly understood as by one of ordinary skill in the art to which the invention belongs, unless otherwise defined. While the invention has been described with respect to a limited number of embodiments, these should not be construed as limitations on the scope of the invention, but rather as exemplifications of some of the preferred embodiments. Other possible variations, modifications, and applications are also within the scope of the invention. Accordingly, the scope of the invention should not be limited by what has thus far been described, but by the appended claims and their legal equivalents.

The invention claimed is:

1. A method for positioning and orienting an ultrasound probe, the method comprising:

receiving a dataset derived from the ultrasound probe, wherein the dataset comprises at least one ultrasound image of a heart of a subject obtained with associated blood flow information, said associated blood flow information providing information about a cardiac cycle timing of said image;

using an artificial intelligence process trained on ultrasound images of hearts of subjects obtained with associated blood flow information and trained to use said information about the cardiac cycle timing to differentiate between image changes resulting from a change in a probe's position and orientation and image changes resulting from the cardiac cycle of fluid flow, said artificial intelligence process to analyze said at least one ultrasound image and said associated blood flow information by applying said trained differentiation to identify a current position and orientation of the probe relative to a target position and orientation which aligns the probe to correctly acquire a selected view of said heart of said subject; and conveying, to a user of the probe, the current position and orientation of the probe relative to the target position and orientation.

2. The method of claim 1, wherein the dataset is received by monitoring a display in communication with the ultrasound probe.

3. The method of claim 1, wherein the artificial intelligence process also outputs an indication of a quality of an image produced by the ultrasound probe at its current position and orientation, wherein the quality of the image corresponds to whether the selected view has been achieved.

4. The method of claim 1, wherein the conveying comprises generating, based on at least a portion of the dataset, one or more images each comprising one or more visual cues indicating the current position and orientation, and causing a presentation of the one or more images on a display.

5. The method of claim 4, wherein the one or more visual cues comprises at least one of an indication of a type, a direction, and a measure of motion required to bring the probe from its current position and orientation to its target position and orientation.

6. The method of claim 1, wherein the conveying comprises presenting an image quality indication scale on a display.

7. A method for correcting a position and orientation of an ultrasound probe, the method comprising:

receiving an image of a heart of a subject derived from the ultrasound probe, wherein the image is superimposed with fluid flow information obtained together with said image, said fluid flow information providing information about a cardiac cycle timing of said image;

using an artificial intelligence process trained on ultrasound images of hearts of subjects obtained with associated fluid flow information to analyze said at least one image and said associated fluid flow information and trained to use said information about the cardiac cycle timing to differentiate between image changes resulting from a change in a probe's position and orientation and image changes resulting from the cardiac cycle of fluid flow, said artificial intelligence process to apply said trained differentiation to determine a current position and orientation of the probe relative to a target position and orientation which aligns the probe to correctly acquire a selected view of said heart of said subject; and conveying, to a user of the probe: the current position and orientation of the probe relative to the target position and orientation; and an indication of a quality of the image as being the selected view.

8. A system for positioning and orienting an ultrasound probe, the system comprising:

a computer processor; and a memory comprising one or more sets of instructions which, when executed, cause the computer processor to:

receive a dataset derived from the ultrasound probe, wherein the dataset comprises at least one ultrasound image of a heart of a subject obtained with associated blood flow information obtained together, said blood flow information providing information about a cardiac cycle timing of said image;

use an artificial intelligence process trained on ultrasound images of hearts of subjects obtained with associated blood flow information and trained to use said information about the cardiac cycle timing to differentiate between image changes resulting from a change in a probe's position and orientation and image changes resulting from the cardiac cycle of fluid flow to apply said trained differentiation to identify a current position and orientation of the probe relative to a target position and orientation which aligns the probe to correctly acquire a selected view of said heart of said subject; and convey, to a user of the probe, the current position and orientation of the probe relative to the target position and orientation.

9. The system of claim 8, wherein the artificial intelligence process also outputs an indication of a quality of an image produced by the ultrasound probe at its current position and orientation, wherein the quality of the image corresponds to whether the selected view has been achieved.

10. The system of claim 8, wherein the conveying comprises generating, based on at least a portion of the dataset, one or more images each comprising one or more visual cues indicating the current position and orientation of the probe; and causing a presentation of the one or more images on a display.

11. The system of claim 10, further comprising displaying an image quality indication scale.

12. The system of claim 10, wherein the one or more visual cues comprises at least one of an indication of a type, a direction, and a measure of motion required to bring the probe from its current position and orientation to its target position and orientation.

* * * * *